(12) United States Patent
Narayanaswamy et al.

(10) Patent No.: US 12,290,389 B2
(45) Date of Patent: May 6, 2025

(54) DISTRIBUTED DATA COLLECTION FOR LARGE FIELD OF VIEW POSITRON EMISSION TOMOGRAPHY

(71) Applicant: GE Precision Healthcare LLC, Wauwatosa, WI (US)

(72) Inventors: Mahesh Raman Narayanaswamy, Milwaukee, WI (US); Mark David Fries, Germantown, WI (US); Jorge Uribe, Waukesha, WI (US); Avichay Bdolah, Burgata (IL); Avihai Radi, Rehovot (IL)

(73) Assignee: GE Precision Healthcare LLC, Wauwatosa, WI (US)

( * ) Notice: Subject to any disclaimer, the term of this patent is extended or adjusted under 35 U.S.C. 154(b) by 224 days.

(21) Appl. No.: 18/090,126

(22) Filed: Dec. 28, 2022

(65) Prior Publication Data
US 2024/0215933 A1 Jul. 4, 2024

(51) Int. Cl.
*A61B 6/03* (2006.01)
*G01T 1/29* (2006.01)

(52) U.S. Cl.
CPC ............ *A61B 6/037* (2013.01); *G01T 1/2985* (2013.01)

(58) Field of Classification Search
CPC .. A61B 6/03; A61B 6/037; G01T 1/29; G01T 1/2985
See application file for complete search history.

(56) References Cited

U.S. PATENT DOCUMENTS

| | | |
|---|---|---|
| 7,180,074 B1 | 2/2007 | Crosetto |
| 9,476,994 B2 | 10/2016 | Zhang et al. |
| 9,632,187 B2 | 4/2017 | Badawi et al. |
| 10,799,200 B2 | 10/2020 | Zhang et al. |
| 2022/0142594 A1 | 5/2022 | Yamazaki |

OTHER PUBLICATIONS

Cheng et al., "Field-Programable-Gate-Array-Based Distributed Coincidence Processor for High Count-Rate Online Positron Emission Tomography Coincidence Data Acquisition," Physics in Medicine & Biology, vol. 66, 2021, 11 pgs.

*Primary Examiner* — Jurie Yun
(74) *Attorney, Agent, or Firm* — Fletcher Yoder, P.C.

(57) ABSTRACT

A distributed data collection architecture for a PET system includes a plurality of data collection boards, wherein each data collection board is coupled to a respective gantry segment of the PET system. The PET system includes a modular gantry having a plurality of gantry segments that are physically separate from each other, and each gantry segment includes a plurality of detector modules coupled to a respective data collection board. Each respective data collection board is configured to acquire all detector event data from a respective plurality of detector modules of the respective gantry segment the respective data collection board is coupled to. Only one data collection board of the plurality of data collection boards is configured to act as a master data collection board that collects all of the detector event data from each data collection board and to generate coincidence pairs from all of the detector event data.

20 Claims, 16 Drawing Sheets

DISTRIBUTED DATA COLLECTION FOR LARGE FIELD OF VIEW POSITRON EMISSION TOMOGRAPHY

BACKGROUND

The subject matter disclosed herein relates to imaging systems, and more particularly to positron emission tomography (PET) imaging systems.

A PET imaging system generates images that represent the distribution of positron-emitting nuclides within the body of a patient. When a positron interacts with an electron by annihilation, the entire mass of the positron-electron pair is converted into two 511 keV photons. The photons are emitted in opposite directions along a line of response. The annihilation photons (known as (2) singles) are detected by detectors that are placed along the line of response on a detector ring. When these photons arrive and are detected at the detector elements at the same time, this is referred to as coincidence or coincidence event (COIN). An image is then generated, based on the acquired data that includes the annihilation photon detection information.

Using a conventional PET scanner, a whole-body scan is acquired by moving the patient bed through a gantry due to conventional PET scanners having a limited field of view (FOV) (e.g., axial FOV or AFOV). This results in a conventional whole-body PET scan typically taking 10 to 30 minutes to acquire sufficient counts for the entire body. To address this issue, more recent PET scanners have increased the AFOV. However, as the AFOV for PET scanners grows larger, the complexity of managing data from the digital detector modules to the rest of the PET imaging system increases.

BRIEF DESCRIPTION

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In one embodiment, a distributed data collection architecture for a PET imaging system is provided. The distributed data collection architecture includes a plurality of data collection boards, wherein each data collection board of the plurality of data collection boards is coupled to a respective gantry segment of the PET imaging system. The PET imaging system includes a modular gantry having a plurality of gantry segments that are physically separate from each other, and each gantry segment of the plurality of gantry segments includes a plurality of detector modules coupled to a respective data collection board of the plurality of data collection boards. Each respective data collection board of the plurality of data collection boards is configured to acquire all detector event data from a respective plurality of detector modules of the respective gantry segment the respective data collection board is coupled to. Only one data collection board of the plurality of data collection boards is configured to act as a master data collection board that collects all of the detector event data from each data collection board of the plurality of data collection boards and to generate coincidence pairs from all of the detector event data.

In another embodiment, a PET imaging system is provided. The PET imaging system includes a modular gantry including a plurality of gantry segments that are physically separate from each other, wherein each gantry segment of the plurality of gantry segments includes a plurality of detector modules. The PET imaging system also includes a distributed data collection architecture including a plurality of data collection boards. Each respective data collection board of the plurality of data collection boards is coupled to a respective plurality of detector modules of a respective gantry segment of the plurality of gantry segments. Each respective data collection board includes a mezzanine board, each mezzanine board has a common hardware structure. Only one data collection board of the plurality of data collection boards is configured to act as a master data collection board that collects all detector event data from each data collection board of the plurality of data collection boards and to generate coincidence pairs from all of the detector event data.

In a further embodiment, a set of data collection boards for a distributed data collection architecture for a PET imaging system is provided. The set of data collection boards includes a first data collection board configured to couple to a first plurality of detector modules of a first gantry segment of the PET imaging system. The PET imaging system includes a modular gantry having a plurality of gantry segments that are physically separate from each other, and the first data collection board includes a first mezzanine board. The set of data collection boards also includes a second data collection board configured to couple to a second plurality of detector modules of a second gantry segment of the PET imaging system. The second data collection board includes a second mezzanine board having a same hardware architecture as the first mezzanine board. The first data collection board is configured to acquire all detector event data from the first plurality of detector modules, and the second data collection board is configured to acquire all detector event data from the second plurality of detector modules, to collect all the detector event data from the first plurality of detector modules via the first data collection board, and to generate coincidence pairs from all of the detector event data from the first plurality of detector modules from all of the detector event data.

BRIEF DESCRIPTION OF THE DRAWINGS

These and other features, aspects, and advantages of the present subject matter will become better understood when the following detailed description is read with reference to the accompanying drawings in which like characters represent like parts throughout the drawings, wherein.

DETAILED DESCRIPTION

Figure 1:
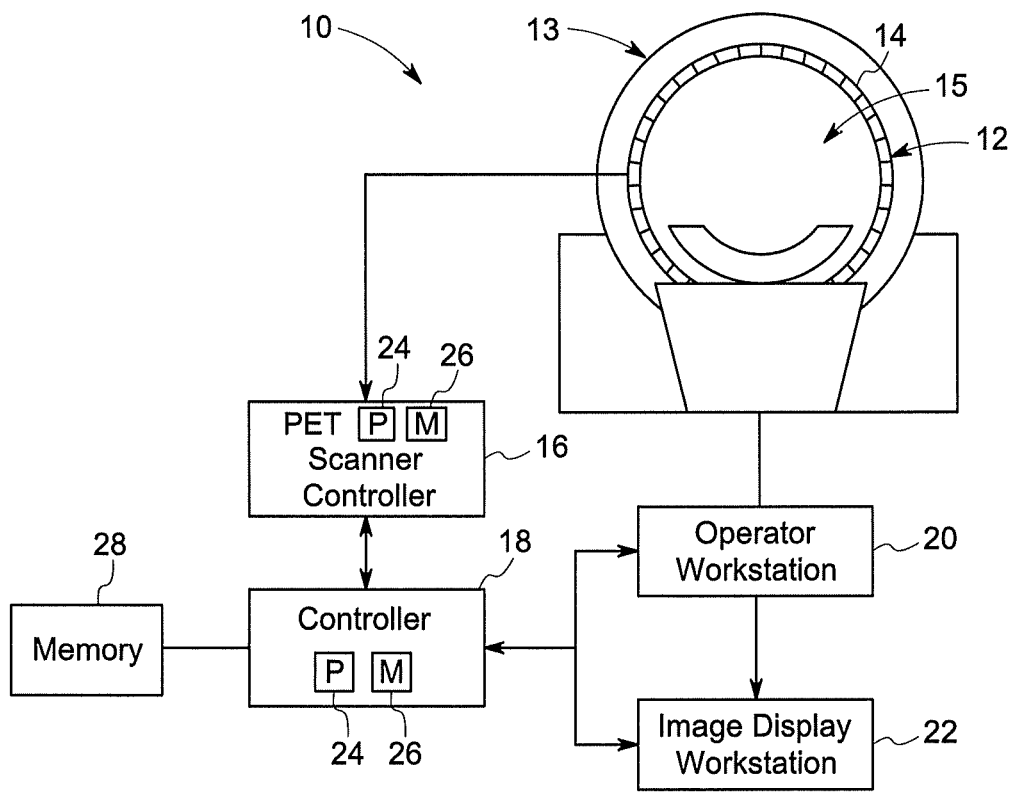
FIG. 1 is a diagrammatical representation of an embodiment of a positron emission tomography (PET) imaging system, in accordance with aspects of the present disclosure.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

Various embodiments provide a distributed data collection architecture for a PET imaging system. The PET imaging system may include a modular gantry made of a plurality of gantry segments (e.g., gantry modules) with each gantry segment having a plurality of detector modules. In addition, each gantry segment is physically separate from the other gantry segments. The distributed data collection architecture may include a plurality of data collection boards. Each data collection board is coupled to a respective gantry segment. More specifically, the respective plurality of detector modules of each respective gantry segment is coupled to a respective data collection board. Each respective data collection board is configured to acquire (e.g., aggregate) all detector event data (e.g., including singles) from the respective plurality of detector of the respective gantry segment the respective data collection board is coupled to. Only one data collection board of the plurality of data collection boards acts as a master data collection board. The master data collection board (besides acquiring the detector event data from the detector modules of the gantry segment it is coupled to) collects all of the detector event data from each data collection board and generates coincidence pairs from all of the detector event data. Each data collection board includes a mezzanine board. Each mezzanine board shares or has a common hardware structure. In certain embodiments, each data collection board (except the master data collection board) includes the mezzanine board coupled to a carrier board. Although the data collection boards are structurally similar with regard to the mezzanine board, the data collection boards may vary as to how and which hardware on the mezzanine board is utilized.

The data collection boards may be electrically coupled in a daisy-chain architecture. In addition, detector modules in adjacent detector rings of a gantry segment may be electrically coupled in a daisy-chain architecture. Each data collection board is configured so that all outputs are outputted directly from the mezzanine board. In certain embodiments, at least one data collection board (in addition to the master data collection board) is configured to perform coincidence event sorting on the detector event data acquired from the respective gantry segment that the at least one data collection board is coupled to. In certain embodiments, only the master data collection board is configured to perform coincidence event sorting on all of the detector event data collected from each data collection board. In certain embodiments, each data collection board is configured to distribute power to the respective plurality of detectors modules of the respective gantry segment that the respective data collection board is coupled to. In certain embodiments, to synchronize operations during a PET scan, the master data collection board is configured to provide (e.g., via its mezzanine board) a system-wide clock signal to the other data collection boards, while each of the other data collection boards is configured to provide (e.g., via their respective mezzanine boards) the system-wide clock signal to the respective plurality of detector modules of the respective gantry segment that the respective other data collection board is coupled to. The disclosed embodiments provide a scalable data collection architecture between multiple sets of detector modules and data aggregation circuit boards that enable a simplified data flow as PET scanners grow larger in the axial FOV.

With the foregoing in mind and turning now to the drawings, FIG. 1 depicts a PET imaging system 10 operating in accordance with certain aspects of the present disclosure. The PET imaging system of FIG. 1 may be utilized with a dual-modality imaging system such as a PET/CT imaging or PET/MRI imaging.

Returning now to FIG. 1, the depicted PET imaging system 10 includes a detector array 12. The detector array 12 of the PET imaging system 10 typically includes a number of detector modules or detector channels (generally designated by reference numeral 14) arranged in one or more rings, as depicted in FIG. 1. Each detector module may include a scintillator block and a photomultiplier tube (PMT) or other light sensor (e.g. silicon photomultiplier). The PET imaging system 10 includes a gantry 13 that is configured to support a full ring annular detector array 12 thereon. As described in greater detail below, the gantry 13 is a modular gantry assembled from multiple gantry segments (e.g., gantry modules) that enables the size (i.e., length) of the gantry 13 to be scalable and the axial FOV of the PET imaging system 10 to be increased. The detector array 12 is positioned around the central opening/bore 15 and can be controlled to perform a normal "emission scan" in which positron annihilation events are counted. To this end, the detector modules 14 forming the detector array 12 generally generate intensity output signals corresponding to each annihilation photon.

The depicted PET imaging system 10 also includes a PET scanner controller 16, a controller 18, an operator workstation 20, and an image display workstation 22 (e.g., for displaying an image). In certain embodiments, the PET scanner controller 16, controller 18, operator workstation 20, and image display workstation 22 may be combined into a single unit or device or fewer units or devices.

The PET scanner controller 16, which is coupled to the detector array 12, may be coupled to the controller 18 to enable the controller 18 to control operation of the PET scanner controller 16. Alternatively, the PET scanner controller 16 may be coupled to the operator workstation 20 which controls the operation of the PET scanner controller 16. In operation, the controller 18 and/or the workstation 20 controls the real-time operation of the PET imaging system 10. One or more of the PET scanner controller 16, the controller 18, and/or the operation workstation 20 may include a processor 24 and/or memory 26. In certain embodiments, the PET imaging system 10 may include a separate memory 28. The detector 12, PET scanner controller 16, the controller 18, and/or the operation workstation 20 may include detector acquisition circuitry for acquiring image data from the detector array 12 and image reconstruction and processing circuitry for image processing. The circuitry may include specially programmed hardware, memory, and/or processors.

The processor 24 may include multiple microprocessors, one or more "general-purpose" microprocessors, one or more special-purpose microprocessors, and/or one or more application specific integrated circuits (ASICS), system-on-chip (SoC) device, or some other processor configuration. For example, the processor 24 may include one or more reduced instruction set (RISC) processors or complex instruction set (CISC) processors. The processor 24 may execute instructions to carry out the operation of the PET imaging system 10. These instructions may be encoded in programs or code stored in a tangible non-transitory computer-readable medium (e.g., an optical disc, solid state device, chip, firmware, etc.) such as the memory 26, 28. In certain embodiments, the memory 26 may be wholly or partially removable from the controller 16, 18.

By way of example, PET imaging is primarily used to measure metabolic activities that occur in tissues and organs and, in particular, to localize aberrant metabolic activity. In PET imaging, the patient is typically injected with a solution that contains a radioactive tracer. The solution is distributed and absorbed throughout the body in different degrees, depending on the tracer employed and the functioning of the organs and tissues. For instance, tumors typically process more glucose than a healthy tissue of the same type. Therefore, a glucose solution containing a radioactive tracer may be disproportionately metabolized by a tumor, allowing the tumor to be located and visualized by the radioactive emissions. In particular, the radioactive tracer emits positrons that interact with and annihilate complementary electrons to generate pairs of annihilation photons. In each annihilation reaction, two annihilation photons traveling in opposite directions are emitted. In a PET imaging system 10, the pair of annihilation photons are detected by the detector array 12 configured to ascertain that two annihilation photons detected sufficiently close in time are generated by the same annihilation reaction. Due to the nature of the annihilation reaction, the detection of such a pair of annihilation photons may be used to determine the line of response (LOR) along which the annihilation photons traveled before impacting the detector, allowing localization of the annihilation event to that line. By detecting a number of such annihilation photon pairs, and calculating the corresponding lines traveled by these pairs, the concentration of the radioactive tracer in different parts of the body may be estimated and a tumor, thereby, may be detected. Therefore, accurate detection and localization of the annihilation photons forms a fundamental and foremost objective of the PET imaging system 10.

Figure 2:
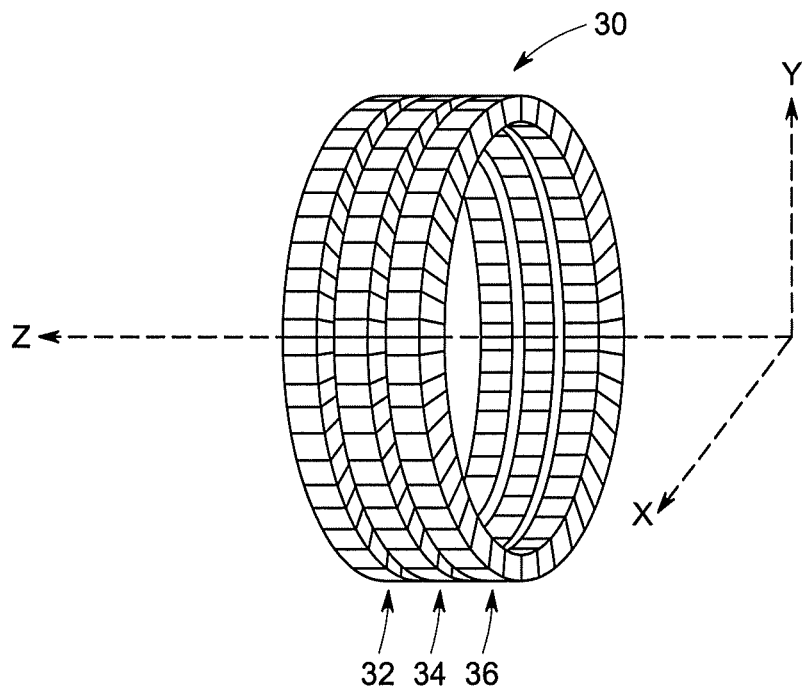
FIG. 2 is a schematic of an embodiment of a 3-D PET scanner, in accordance with aspects of the present disclosure.

Data associated with coincidence events along a number of LORs may be collected and further processed to reconstruct two-dimensional (2-D) tomographic images. Most modern PET scanners can operate in a 3-D mode, where coincidence events from different detector rings positioned along the axial direction are counted to obtain 3-D tomographic images. For example, a PET scanner 30 with multiple detector rings is shown in FIG. 2, where the individual detectors and photosensors are not shown. As shown, the PET scanner 30 includes three detector rings 32, 34 and 36. The number of detector rings may vary (e.g., 2, 3, 4, 5, or more detector rings). In the disclosed embodiments, coincidence events may occur in different detector rings of different gantry segments of the modular gantry along the axial direction.

Figure 3:
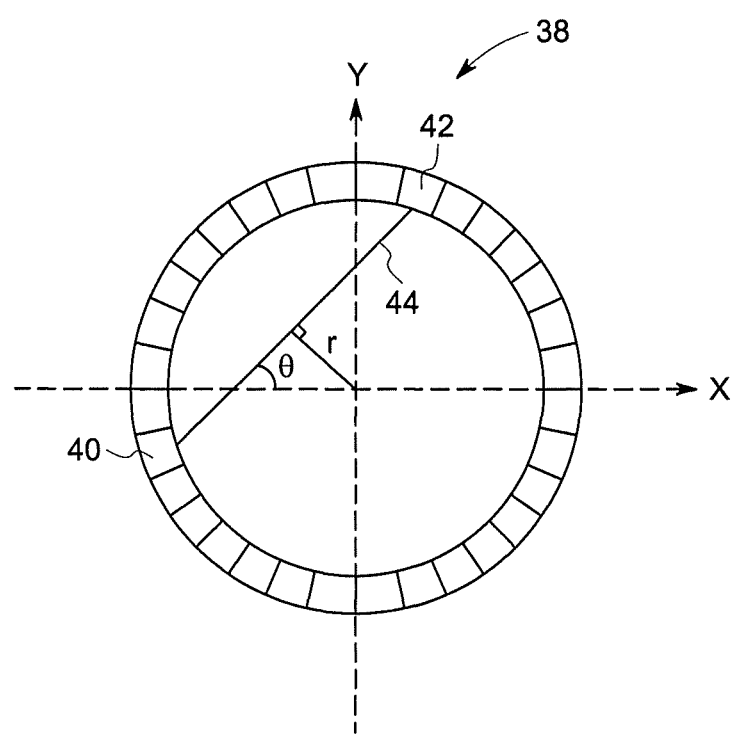
FIG. 3 is a schematic of a line of response (LOR) in a PET imaging system, in accordance with aspects of the present disclosure.

Traditionally, data associated with coincidence events are stored in the form of sinograms based on their corresponding LORs. For example, in a 2-D PET scanner 38 like the one illustrated in FIG. 3, if a pair of coincidence events are detected by two opposite detectors 40 and 42, an LOR may be established as a straight line 44 linking the two detectors 40, 42. This LOR may be identified by two coordinates (r, θ), wherein r is the radial distance of the LOR from the center axis of the detector ring 30, and θ is the trans-axial angle between the LOR and the X-axis. The detected coincidence events may be recorded in a 2-D matrix λ(r, θ). As the PET scanner continues to detect coincidence events along various LORs, these events may be binned and accumulated in their corresponding elements in the matrix λ(r, θ). The result is a 2-D sinogram λ(r, θ), each element of which holds an event count for a specific LOR. In a 3-D PET scanner, an LOR is defined by four coordinates (r, θ, φ, z), wherein the third coordinate φ is the axial angle between the LOR and the center axis (or Z-axis as shown in FIG. 2) of the detector rings and z is the distance of the LOR from the center of the detector along the Z-axis. Typically the third and fourth co-ordinates are combined into only one variable, v, which can define both φ and z coordinates. In this case, the detected coincidence events are stored in a 3-D sinogram λ(r, θ, v).

Figure 4:
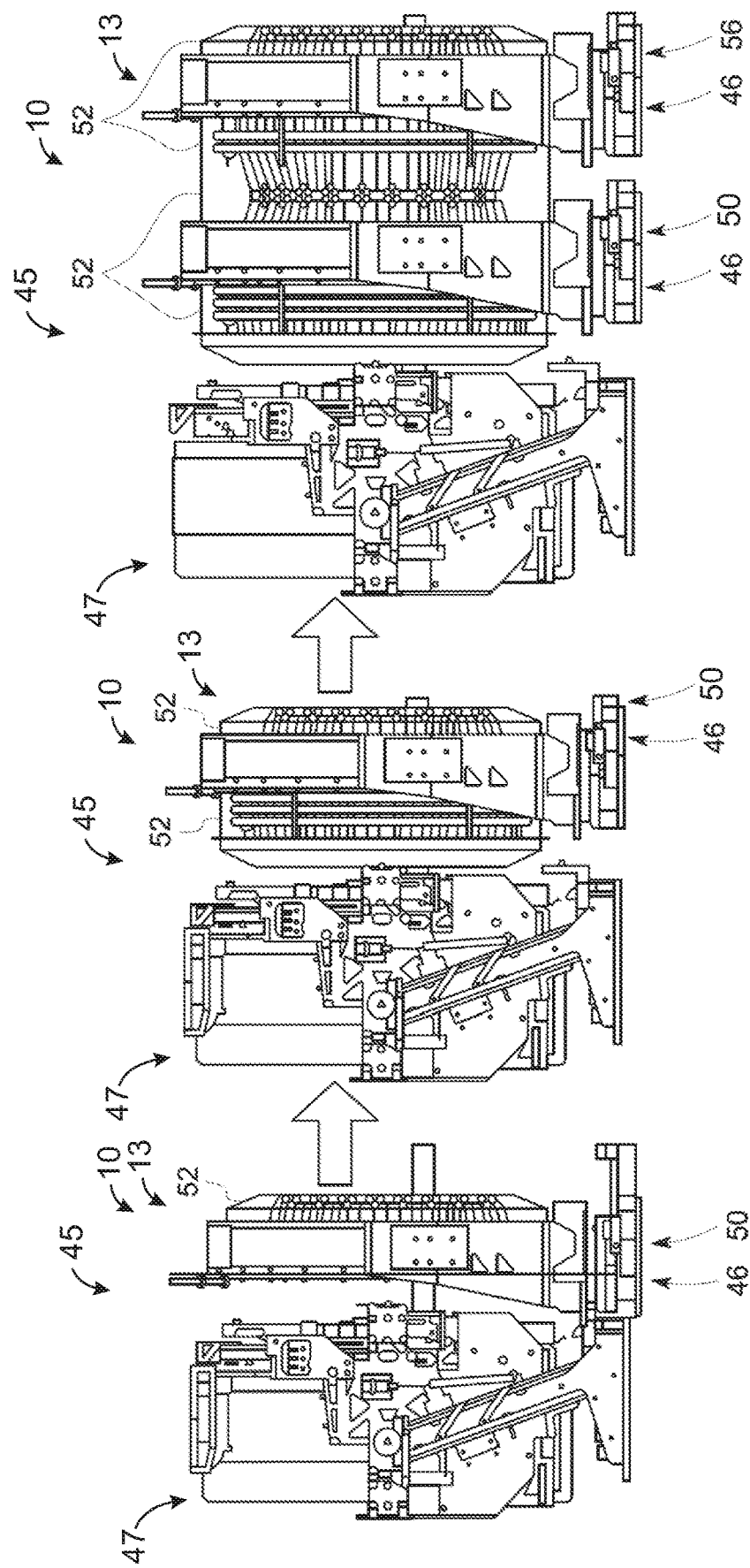
FIG. 4 is a schematic view of a computed tomography (CT)-PET imaging system including a modular gantry of a PET imaging system having gantry segments added, in accordance with aspects of the present disclosure.
Figure 5A:
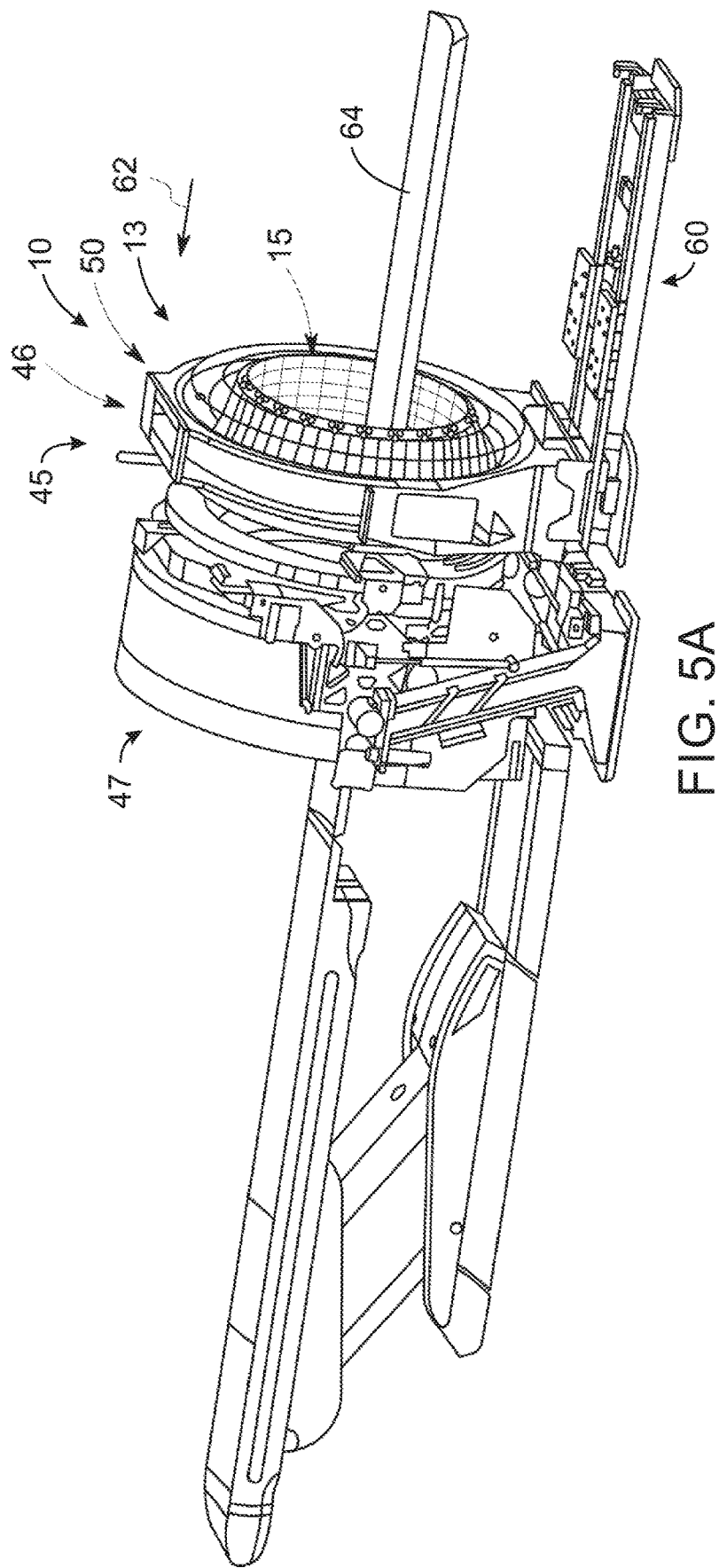
FIGS. 5A-5D are perspective views of different CT-PET imaging systems with the PET imaging systems having different AFOVs, in accordance with aspects of the present disclosure.
Figure 5B:
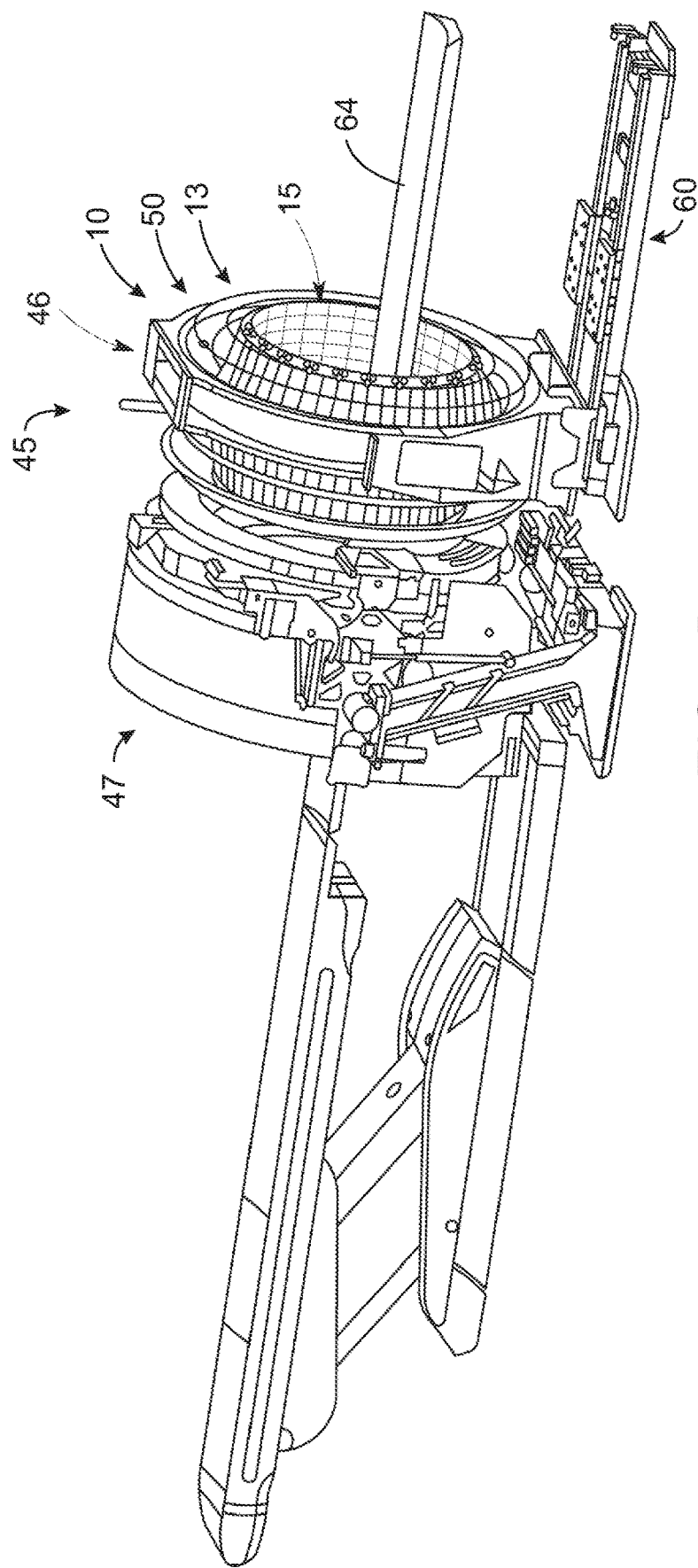
Figure 5C:
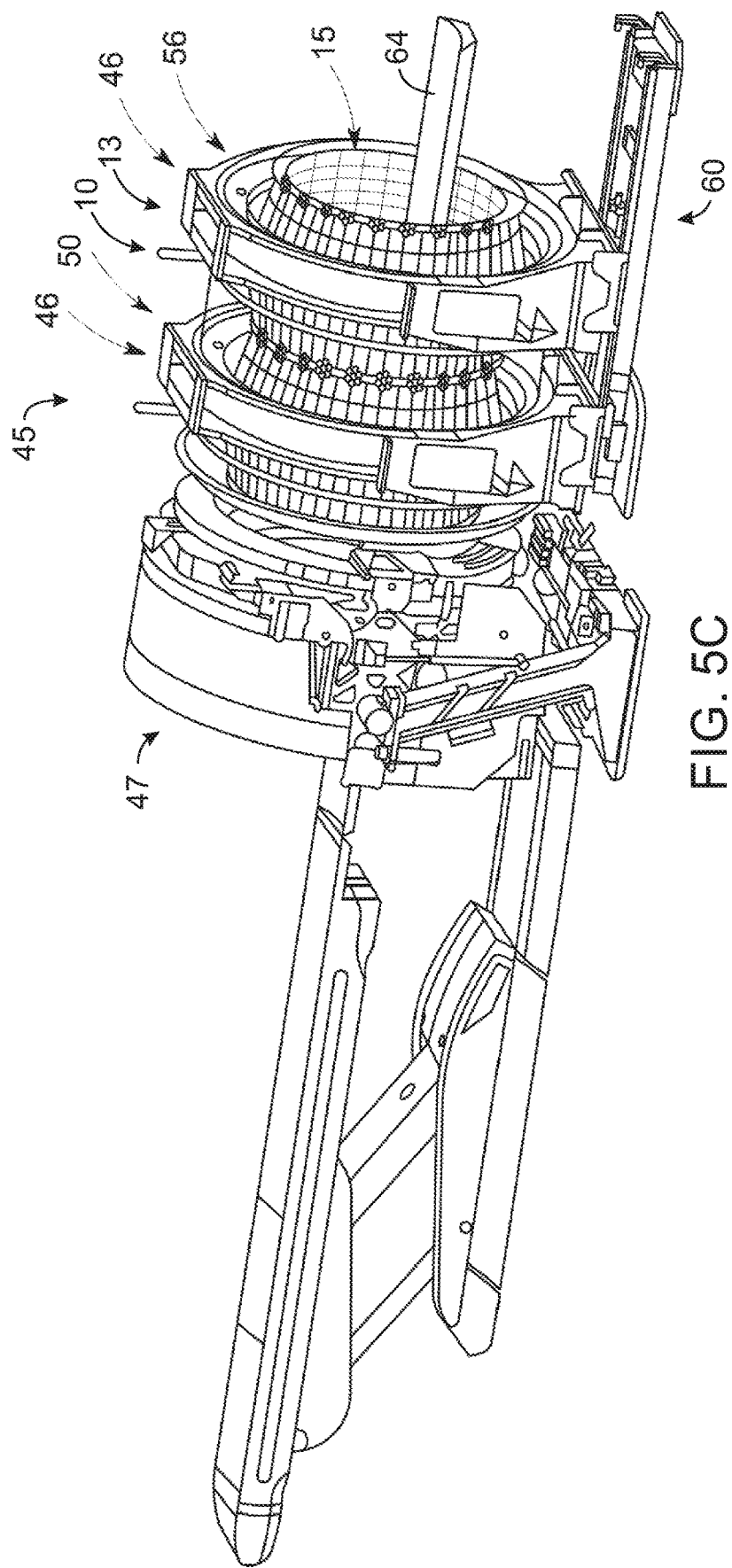
Figure 5D:
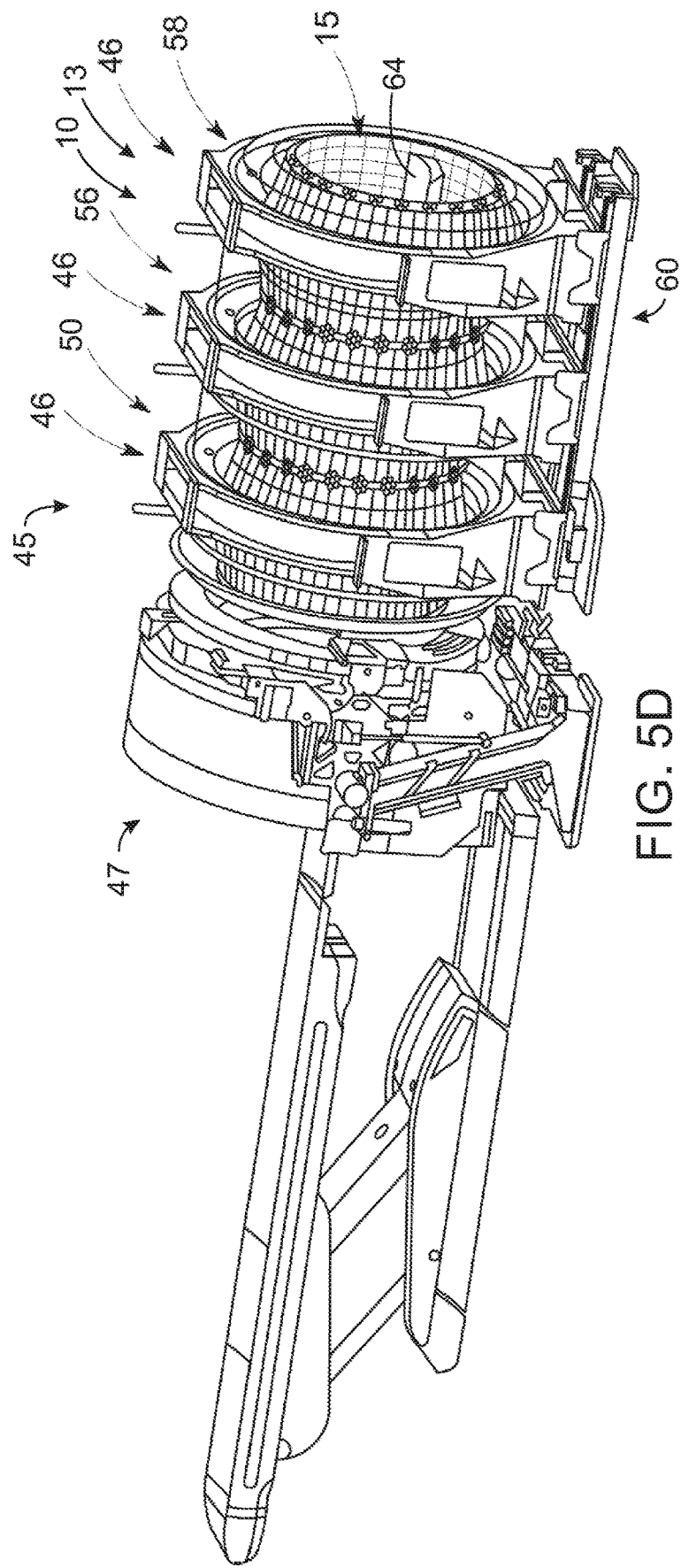

FIG. 4 is a schematic view of a computed tomography (CT)-PET imaging system 45 including the modular gantry 13 of the PET imaging system 10 having gantry segments or modules 46 added or assembled to form the modular gantry 13. FIGS. 5A-5D are perspective views of different CT-PET imaging systems 45 with the PET imaging systems 10 having different FOVs due to a size or a length of the modular gantry 13. The gantry segments 46 are physically separate from each other. As depicted in FIGS. 4 and 5 the modular gantry 13 of the PET imaging systems 10 are coupled to a CT gantry 47. In certain embodiments, the modular gantry 13 of the PET imaging system 10 (having one or more gantry segments 46) is not coupled to a CT gantry 47 (i.e., standalone PET imaging system 10). As depicted in FIGS. 4 and 5, the PET imaging system 10 has an initial gantry segment 50 as the minimum configuration of said PET imaging system 10. In this embodiment, the gantry segment 50 has an axial FOV of 32 centimeters (cm)

and a single ring 52 of detector modules as depicted in FIGS. 4 and 5A. In certain embodiments, an additional gantry ring of detector modules having an axial FOV of 32 cm and may be coupled to the initial gantry segment 50 to further increase an axial FOV (e.g., 640 mm axial FOV) of the PET imaging system 10 as depicted in FIGS. 4 and 5B. In certain embodiments, a further gantry segment 56 (e.g., also having an axial FOV of 64 cm and two rings 52 of detector modules) may be coupled to the gantry segment 50 to even further increase an axial FOV (e.g., 1284 mm axial FOV) of the PET imaging system 10 as depicted in FIGS. 4 and 5C. In certain embodiments, a still further gantry segment 58 may be coupled to the gantry segments 50, 56 to still further increase an axial FOV of the PET imaging system 10 in FIGS. 4 and 5D.

In certain embodiments, the modular gantry 13 of the PET imaging system 10 is scalable by gantry segments 46 each having two rings 52 of detector modules and an axial FOV of 64 cm. In certain embodiments, the gantry segments 46 may include a different FOV and the modular gantry 13 may be scaled differently (e.g., by gantry segments 46 of 32 cm). Gantry segments 46 may be assembled together to achieve an axial FOV of up to at least 256 cm. The modularity of the gantry 13 enables better serviceability. The gantry segments 46 are assembled together utilizing a guide system 60 (depicted in FIGS. 5A-5D) that enables each gantry segment 46 to slide (as indicate by arrow 62 in FIG. 5A) until it contacts and is coupled to another gantry segment 46.

Each ring 52 of detector modules may include 24 to 26 detector modules. The bore 15 of each gantry segment 46 (as depicted in FIGS. 5A-5D) may have a diameter of 75 to 80 cm. As depicted in FIGS. 5A-5D, a support 64 (e.g., table) may be utilized to extend a patient into the bore 15 of the modular gantry 13 for imaging. The PET imaging system 10 is configured to perform a dynamic whole-body PET scan.

Figure 6:
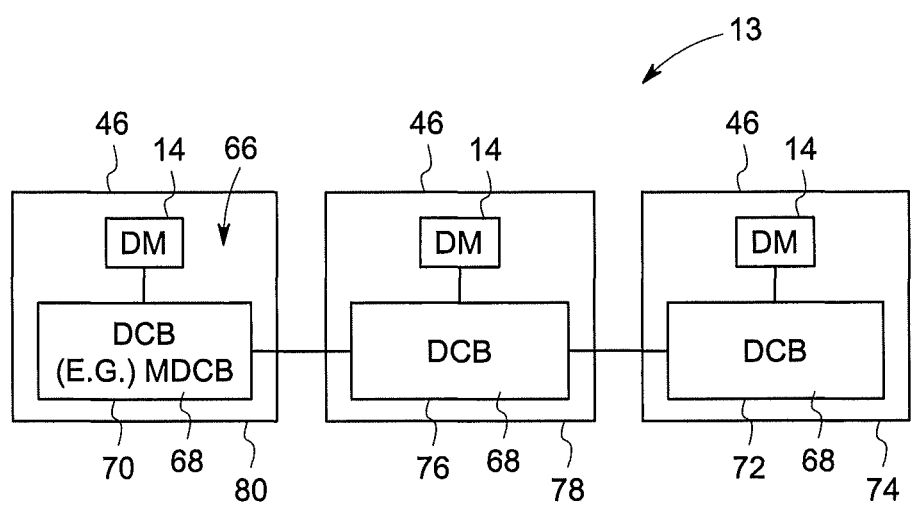
FIG. 6 is a schematic view of a distributed data collection architecture coupled to a modular gantry, in accordance with aspects of the present disclosure.

FIG. 6 is a schematic view of a distributed data collection architecture 66 coupled to the modular gantry 13. Besides the modular gantry 13 being scalable to increase the axial FOV, the distributed data collection architecture 66 is also scalable. The distributed nature and the scalability of the distributed data collection architecture 66 provides for reliable data collection and processing as the axial FOV of the PET imaging system increases.

As depicted in FIG. 6, each gantry segment 46 includes a data collection board 68. Each data collection board 68 is coupled to each detector module 14 of the respective gantry segment 46 the data collection board 68 is coupled to. Each data collection board 68 acquires (e.g., aggregates) all detector event data (e.g. including singles) from the detector modules 14 of its corresponding gantry segment 46. Thus, each data collection board 68 acts as an aggregator data collection board. The plurality of data collection boards 68 is coupled via a daisy-chain architecture. In certain embodiments, the respective detector modules 14 of each gantry segment 46 may also be electrically coupled via daisy-chain architecture.

Only one data collection of the plurality of data collection boards acts or serves as a master data collection board 70. Each data collection board 68 has the capability to be a master collection board 70 for a separate 64 cm FOV processing. The master data collection board 70 (besides acquiring the detector event data from the detector modules 14 of the gantry segment 46 it is coupled to) collects all of the detector event data from each of the other data collection boards 68 and generates coincidence pairs from all of the detector event data. For example, data collection board 72 only acquires (e.g., aggregates) detector event data from the detector modules 14 of its corresponding gantry segment 46 (e.g., gantry segment 74). Data collection board 76 acquires (e.g., aggregates) detector event data from the detector modules 14 of its corresponding gantry segment 46 (e.g., gantry segment 78) and collects all detector event data acquired by the data collection board 68 coupled to the detector modules 14 of the gantry segment 74. The master data collection board 70 acquires (e.g., aggregates) detector event data from the detector modules 14 of its corresponding gantry segment 46 (e.g., gantry segment 80) and collects all detector event data acquired by the data collection boards 72, 76 coupled to the detector modules 14 of the respective gantry segments 74, 78.

As described in greater detail below, each data collection board 68 (including the master data collection board 70) includes a mezzanine board (e.g., daughter board). Each mezzanine board shares or has a common hardware structure. In certain embodiments, each data collection board 68 includes (except the master data collection board 70) includes the mezzanine board coupled to a carrier board (e.g., motherboard). Although the data collection boards 68 are structurally similar with regard to the mezzanine board, the data collection boards 68 may vary as to how and which hardware on the mezzanine board is utilized.

Each data collection board 68 is configured so that all outputs are outputted directly from the mezzanine board. In certain embodiments, at least one data collection board 68 (in addition to the master data collection board 70) is configured to perform coincidence event sorting on the detector event data acquired from the respective gantry segment 46 that the at least one data collection board 68 is coupled to. In certain embodiments, only the master data collection board 70 is configured to perform coincidence event sorting on all of the detector event data collected from each data collection board 68. In certain embodiments, the master data collection board 70 may also perform other functions related to detector event processing. For example, the master data collection board 70 may perform histogramming on the coincidence event sorted events, throttling (e.g., random dropping of events), and other functions related to coincidence processing.

In certain embodiments, each data collection board 68 is configured to distribute power to the respective plurality of detectors modules 14 of the respective gantry segment 46 that the respective data collection board 68 is coupled to. In certain embodiments, to synchronize operations during a PET scan, the master data collection board 70 is configured to provide (e.g., via its mezzanine board) a system-wide clock signal to the other data collection boards 68, while each of the other data collection boards 68 is configured to provide (e.g., via their respective mezzanine boards) the system-wide clock signal to the respective plurality of detector modules 14 of the respective gantry segment 46 that each respective other data collection board 68 is coupled to. The disclosed embodiments provide a scalable data collection architecture between multiple sets of detector modules and data aggregation circuit boards that enable a simplified data flow as PET scanners grow larger in the axial FOV.

Figure 7:
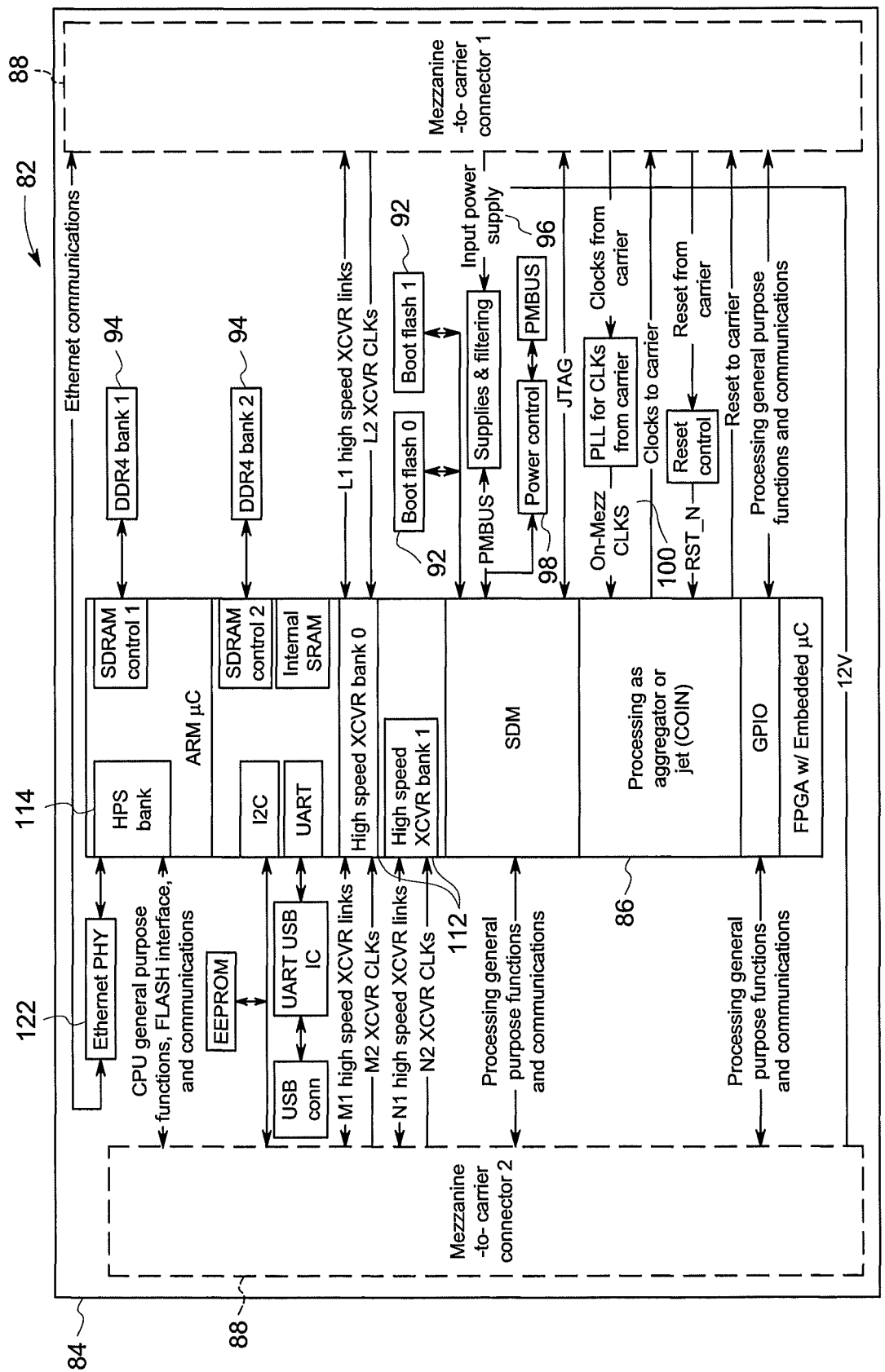
FIG. 7 is a schematic view of a common mezzanine board, in accordance with aspects of the present disclosure.

FIG. 7 is a schematic view of a common mezzanine board 82. The common mezzanine board 82 is utilized by each data collection board (e.g., data collection boards 68 including the master data collection board 70 in FIG. 6). Each mezzanine board 82 of the data collection boards shares or has a common hardware structure. The common hardware structure of the mezzanine board 82 may vary from the structure depicted in FIG. 7 but each mezzanine board 82 of the data collection boards include the same mezzanine board 82.

The mezzanine board 82 includes a printed circuit board 84 on which the hardware is disposed. The mezzanine board 82 includes a field-programmable gate array (FPGA) device 86 configured to couple to transceiver links via connectors 88 (indicated in dashed outline) that couples the carrier board and the mezzanine board 82 to enable communication of data between the mezzanine board 82 and the carrier board. In certain embodiments, the FPGA device 86 may be associated with a hard processor system or ARM processor. The FPGA device 86 utilizes the JTAG industry standard to provide access to their programming features. The mezzanine board 82 may also include a serial port debugger that utilizes the JTAG industry standard to provide access to its debug functions. The mezzanine board 82 further includes a non-volatile computer memory storage medium such as a FLASH memory 92. The mezzanine board 82 even further includes multiple banks of synchronous dynamic random-access memory with a high bandwidth interface such as a Double Data Rate 4 Synchronous Dynamic Random-Access Memory (DDR4 SDRAM) 94. The mezzanine board 82 yet further includes power input 96, via connectors 88 for receiving power. The mezzanine board 82 is configured for power regulation/sequencing 98.

The mezzanine board 82 still further includes a system-wide clock signal generator and clock buffer 100 (e.g., 5 MHz fanout buffer). The mezzanine board 82 includes a plurality of dedicated clock connections via connectors 88. Each clock connection may be configured to communicate with a different data collection board via high-speed data cables. In certain embodiments, when the mezzanine board 82 is the master data collection board it generates the system-wide clock signal via the clock signal generator and buffer 100, and it provides the system-wide clock signal to the other data collection boards via connectors 88. The mezzanine board 82 (whether the master data collection board or one of the other data collection boards) utilizes the clock buffer 100 to provide the system-wide clock signal to the respective detector modules each data collection board is coupled to. When the mezzanine board 82 is part of one of the data collection boards other than the master data collection board, it utilizes the system-wide clock generator and buffer 100 to select the external system-wide clock signal from the master data collection board.

The mezzanine board 82 includes high-speed transceiver banks 112 for communicating to the system host computer of the PET imaging system and/or PET Acquisition and Reconstruction Computer (or Controller) (PARC) (e.g., on the PET scanner controller 16, the controller 18, and/or the operation workstation 20 in FIG. 1) utilizing standard TCP/Ethernet packet-based protocols. The transceivers 112 communicate via connectors 88 to small form-factor pluggable (SFP) transceivers (shown as COIN in FIG. 8) for transmitting coincidence data (i.e., two photons paired together in a coincidence event). The transceivers 112 also communicate via connectors 88 to Ethernet transceivers (shown as PDD in FIG. 8) for transmitting periodic detector data (i.e., data stream with values from various parameters reflecting the "health" of the detector). The uC HPS I/O Bank 114 further includes a subnetwork Ethernet transceiver 122 for communicating command and control data between the mezzanine board 82 and the host (shown as Command-and-Control in FIG. 8).

The mezzanine board 82 also includes transceivers 112 for communicating with other data collection boards utilizing standard Serial Lite 4 packet-based protocols via connectors 88. The transceivers 112 communicate via connectors 88 to quad small form-factor pluggable (QSFP-DD) transceivers (shown in FIG. 8). Different pairs (shown in FIG. 8) of QSFP-DD transceivers are configured to communicate with different data collection boards. All outputs of the data collection boards are outputted directly from the mezzanine board 82 via the transceivers 112.

Although the mezzanine board 82 for each data collection board includes a common hardware structure, the data collection boards may vary as to how and which hardware on its respective mezzanine board 82 is utilized. For example, in a data collection board for certain PET imaging system, the mezzanine board 82 may be utilized for solely transmitting detector event data (e.g., singles) via the transceivers 112 to the system host computer of the PET imaging system and/or PARC host computer. In some PET imaging system, power for the data collection board is received through a carrier board that the mezzanine board 82 is coupled to. In addition, power and data are transferred via Mini-Serial Attached Small Computer System Interface (SAS) connectors on the carrier board between the data collection boards and the detector modules coupled to the respective data collection boards of each gantry segment.

For data collection boards that solely aggregate detector event data (i.e., AGG function and are not the master data collection board), power for the data collection board is received through a carrier board that the mezzanine board 82 is coupled to. In addition, power and data are transferred via Mini-SAS connectors on the carrier board between the data collection boards and the detector modules coupled to the respective data collection boards. Each of the two mezzanine boards 82, performing the aggregator function utilize only one of the QSFP-DD transceivers (as represented by reference numerals 126, 128 in FIG. 8) to transmit detector event data (e.g., singles) to the master data collection board. In this embodiment, the data collection carrier board has a plurality of mezzanine boards 84, one for each set of detector modules of a gantry segment. In this embodiment, there are two sets of detector modules attached to the data collection board via two mezzanine boards 82, one for each set of detector modules of a gantry segment. In this embodiment, there is a third, unpopulated spot for a mezzanine board that serves to create detector coincidence (COIN) data from the singles data from the detector modules. For data collection boards that solely perform the aggregation (AGG) function, this third spot is not needed and is unpopulated.

For data collection boards that both aggregate detector event data (i.e. AGG function) and create coincidence (COIN) data from singles data (i.e., joint event transmitter (JET) function, i.e., taking singles and piping into the master data collection board), these boards service as the master data collection board. In this embodiment, the data collection board has all three mezzanine spots populated. Two spots are populated with a plurality of mezzanine boards 82 that perform the AGG function on two sets of detector modules, one in each of two gantry segments. The third spot is populated with a mezzanine board 82 that performs the COIN generation (JET) function. Each of the two mezzanine boards 82, performing the aggregator function utilize one of the QSFP-DD connectors via transceivers 112 (as shown by reference numerals 126, 128 in FIG. 8) to transmit detector event data (e.g., singles) to the third mezzanine board 82 performing the COIN generation (JET) function, on the master data collection board. Additionally, the third mezzanine board 82, performing the COIN generation (JET) function on the master data collection board, receives aggregated singles data from the previous aggregator data collection boards via one of the QSFP-DD connectors and transceivers 112 (as shown by reference numerals 126, 128 in FIG. 8). The master data collection board utilizes the transceivers 112 to communicate the detector event data (e.g., coincidence pairs) to the system host computer of the PET imaging system and/or PARC.

Figure 8:
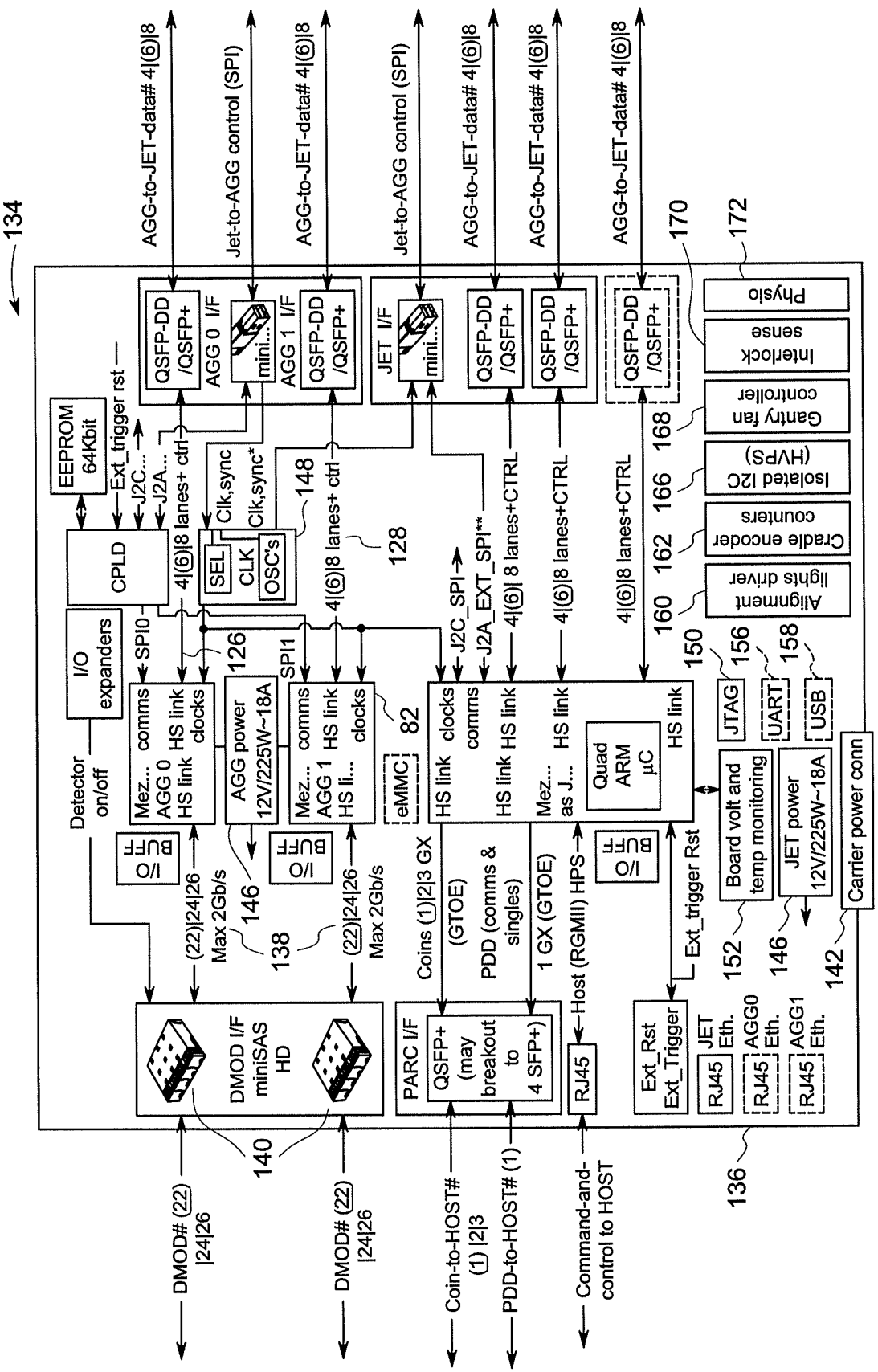
FIG. 8 is a schematic view of a carrier board coupled to the common mezzanine board, in accordance with aspects of the present disclosure.

FIG. 8 is a schematic view of a carrier board 134 to couple to the common mezzanine board. As noted above, data collection boards (other than the master data collection board) include the carrier board 134 coupled to the common mezzanine board. Some of the hardware may vary on the carrier board 134 for different gantry segments. The carrier board 134 includes a printed circuit board 136 on which hardware is disposed. The carrier board 134 includes the mezzanine connectors 88 (shown in FIG. 7) to couple the carrier board 134 and the mezzanine boards and enable the communication of data between the carrier board and the mezzanine board. The connectors 88 are coupled to a plurality of transceiver links 138. The transceiver links 138 are coupled to Mini-SAS connectors 140 that are configured to couple to the detector modules of a gantry segment. The carrier board 134 includes a power connector 142 for receiving power (e.g., from a low voltage supply or a high voltage supply) to power the data circuit board. In certain embodiments, the data collection board (e.g., via the carrier board 134) may distribute power to the detector modules via the Mini-SAS connectors 140.

The carrier board 134 also includes a step-down converter and other voltage regulators 146 to regulate the power supply to the data collection board. The carrier board 134 also includes clock generation and buffers 148 (e.g., 5-MHZ fanout buffer). The carrier board 134 further includes voltage/temperature sensors 152 and an analog-to-digital converter.

The carrier board 134 may include further hardware. For example, the carrier board 134 may include a serial port debugger 150 that utilizes the JTAG industry standard to provide access to its debug functions. The carrier board 134 may further include serial port UART 156 and USB 158 connections, as well as other hardware, to control functions and features such as alignment lights 160, cradle encoder counters 162, power supplies 166, gantry fan controllers 168, system interlock sense devices 170, and physical input/output devices (PHYSIO) 172.

In a data collection board for certain PET imaging system, power for the data collection board is received through the carrier board 134. In addition, power and data is transferred via the Mini-SAS connectors 140 on the carrier board 134 between the data collection boards and the detector modules coupled to the respective data collection boards.

For data collection boards that solely aggregate detector event data (i.e., are not the master data collection board), power for the data collection board is received through the carrier board 134. In addition, power and data is transferred via the Mini-SAS connectors 140 on the carrier board 134 between the data collection boards and the detector modules coupled to the respective data collection boards.

Figure 9:
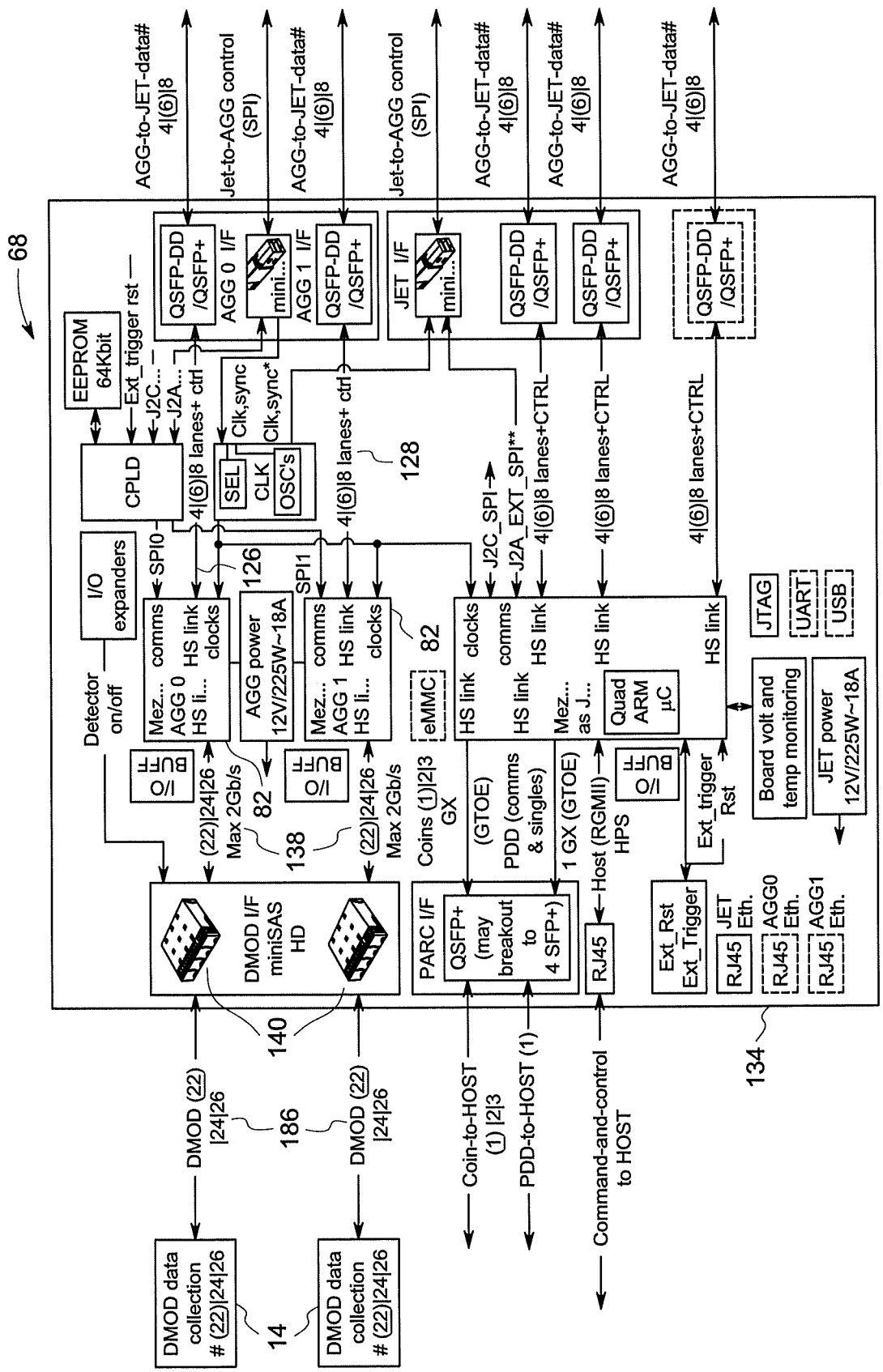
FIG. 9 is a schematic view of a data collection board coupled to detector modules of a gantry segment, in accordance with aspects of the present disclosure.

FIG. 9 is a schematic view of the data collection board 68 (e.g., aggregator data collection board) coupled to detector modules 14 of a gantry segment that the data collection board 68 is coupled to. The data collection board 68 includes the common mezzanine board 82 coupled to the carrier board 134 via the connectors (not shown). The mezzanine board 82 and the carrier board 134 are as described in FIGS. 7 and 8, respectively. The Mini-SAS connectors 140 of the carrier board 134 are coupled to the detector modules 14 of the gantry segment as indicated by the arrows 186. The signal interface between the detector modules 14 and the data collection board 68 is approximately less than 4 gigabits per second (Gbps). Detector event data (e.g., singles events) from the detector modules is communicated to the Mini-SAS connectors 140 and then to the transceiver links 138 of the carrier board 134. In certain embodiments, a GX transceiver with a custom interface wrapper may be utilized to transfer the detector event data of each gantry segment to the carrier board 134. In certain embodiments, the detector event data is transferred to carrier board 134 utilizing direct physical attachment (DirectPHY) packets. In certain embodiments, other packet-based options may be utilized to transfer the detector event data of each gantry segment to the carrier board 134. From the transceiver links 138, the detector event data is communicated to the FPGA 86 (shown in FIG. 7) of the mezzanine board 82 where the data is aggregated. The aggregated detector event data for the gantry segment is then communicated from one of the pairs 126 and 128 of the transceivers 112 (shown in FIG. 7) to the master data collection board via standard Serial Lite 4 packet-based protocols. In certain embodiments, other packet-based options may be utilized to transfer aggregated event data for the gantry segment. Power for the data collection board 68 is received through the carrier board 134. In addition, power is transferred via the Mini-SAS connectors 140 on the carrier board 134 to the detector modules 14.

In certain embodiments, besides aggregating data from the gantry segment it is coupled to, the data collection board 68 also collects data from the data collection board 68 of other data collection boards and passes it on to the master data collection board. In certain embodiments, besides aggregating data from the gantry segment its coupled to, the data collection board 68 may perform coincidence event sorting on the all the detector event data acquired from the gantry segment it is coupled to.

Figure 10A:
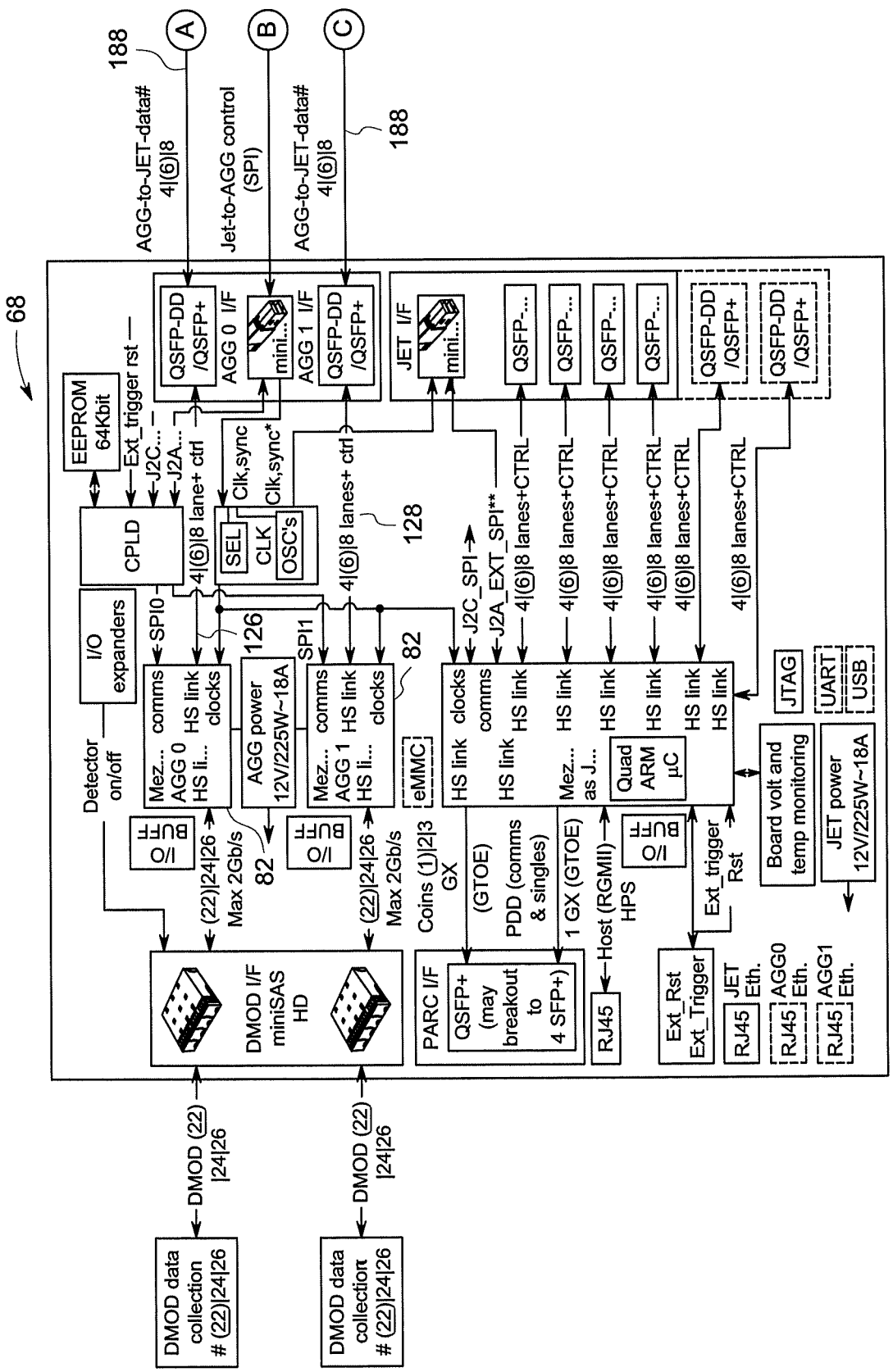
FIGS. 10A and 10B are a schematic view of a data collection board in communication with a master data collection board, in accordance with aspects of the present disclosure.
Figure 10B:
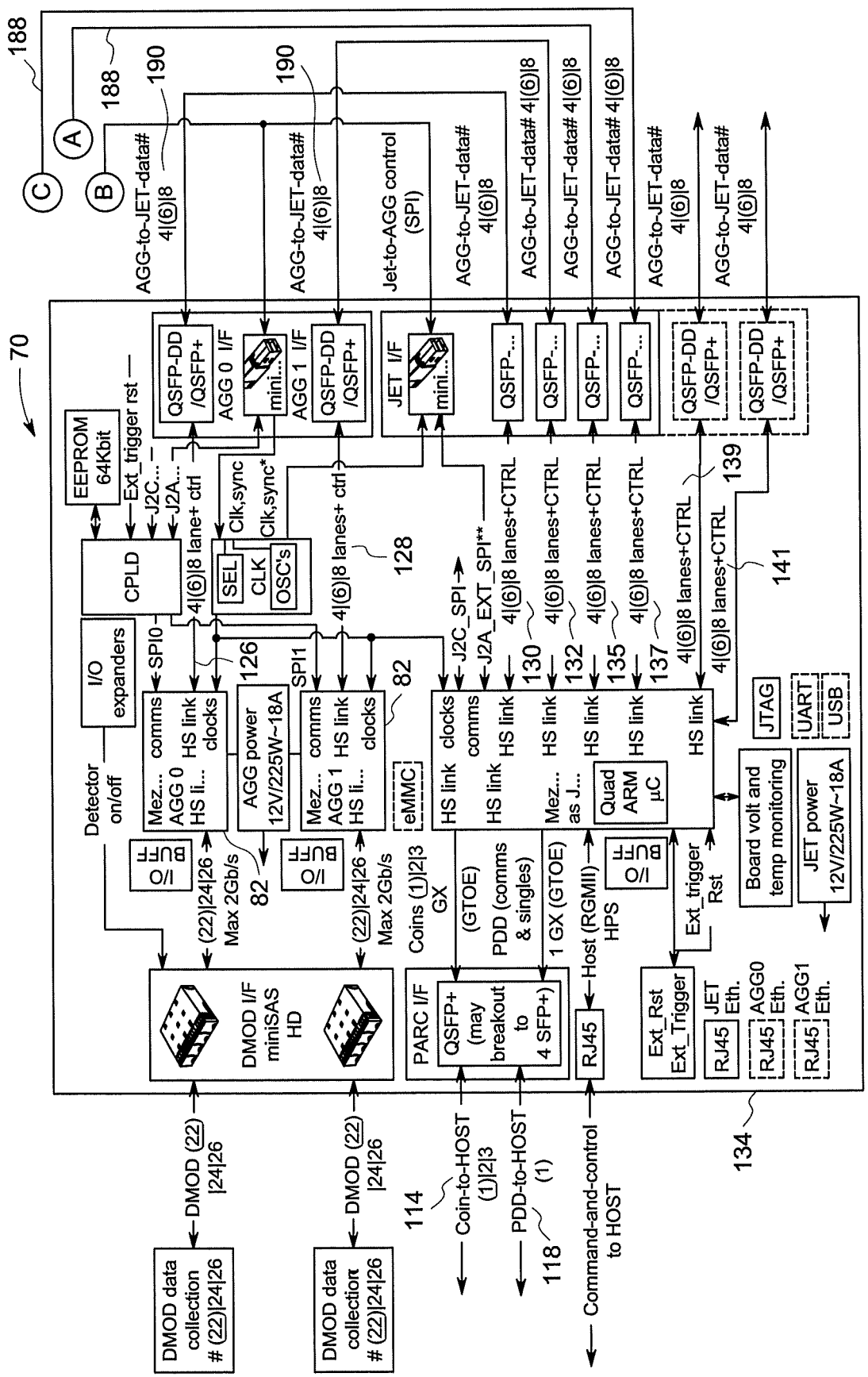

FIGS. 10A and 10B are a schematic view of the data collection board 68 in communication with the master data collection board 70 (e.g., for a modular gantry having two gantry segments and a patient axial FOV of approximately 128 cm). The data collection board 68 and the master data collection board 70 are as described above and each coupled to a respective gantry segment of a modular gantry. The data collection board 68 (e.g., aggregator data collection board) collects the detector event data (e.g., event singles data) from the detector modules of the gantry segment it is coupled to. The master data collection board 70 aggregates or collects the detector event data from the detector modules of the gantry segment it is coupled to. In addition, the master data collection board 70 collects all of detector event data from the data collection board 68. In particular, data collection board 68 communicates the detector event data to the master data collection board 70 via one of its pairs 126 and 128, via transceivers 112 (shown in FIG. 7) on its respective aggregator function mezzanine boards 82 to the corresponding pair, 135 and 137, of transceivers 112 (shown in FIG. 7) of the coincidence (JET) function mezzanine board 82 of the master data collection board 70 via QSFP-DD cables 188. Further, the master data collection board 70 generates coincidence pairs from all of the detector event data collected from the two gantry segments. In addition, the master data collection board 70 collects detector event data from the aggregator function mezzanine boards 82 mounted on its own mezzanine spots. In particular, aggregator function mezzanine boards 82 on the master data collection board 70 send detector event data to the coincidence (JET) function mezzanine board 82, via one of the pairs 126 and 128 on the master data collection board to corresponding pairs 130 and 132, also on the master data collection board. In particular, QSFP-DD cables 190 are used to loop-back the aggregated data from the aggregator function mezzanine boards 82 to the coincidence function mezzanine board 82. The master data collection board 70 transfers or communicates the coincidence data to the system host computer of the PET imaging system and/or PARC via the QSFP+ transceivers 114. The master data collection board 70 also transfers or communicates periodic detector data to the system host computer of the PET imaging system and/or PARC via the QSFP+ transceivers 118.

In certain embodiments, only the master data collection board 70 performs coincidence event sorting on all of the detector event data collected from the two gantry segments. In certain embodiments, the data collection board 68 and the master data collection board 70 both do coincidence event sorting on the respective detector event data collected from the respective detector modules of the respective gantry segments they are coupled to.

The master data collection board 70 may also perform other functions related to detector event processing. For example, the master data collection board 70 may perform histogramming on the coincidence event sorted events, throttling (e.g., random dropping of events), and other functions related to coincidence processing.

Figure 11A:
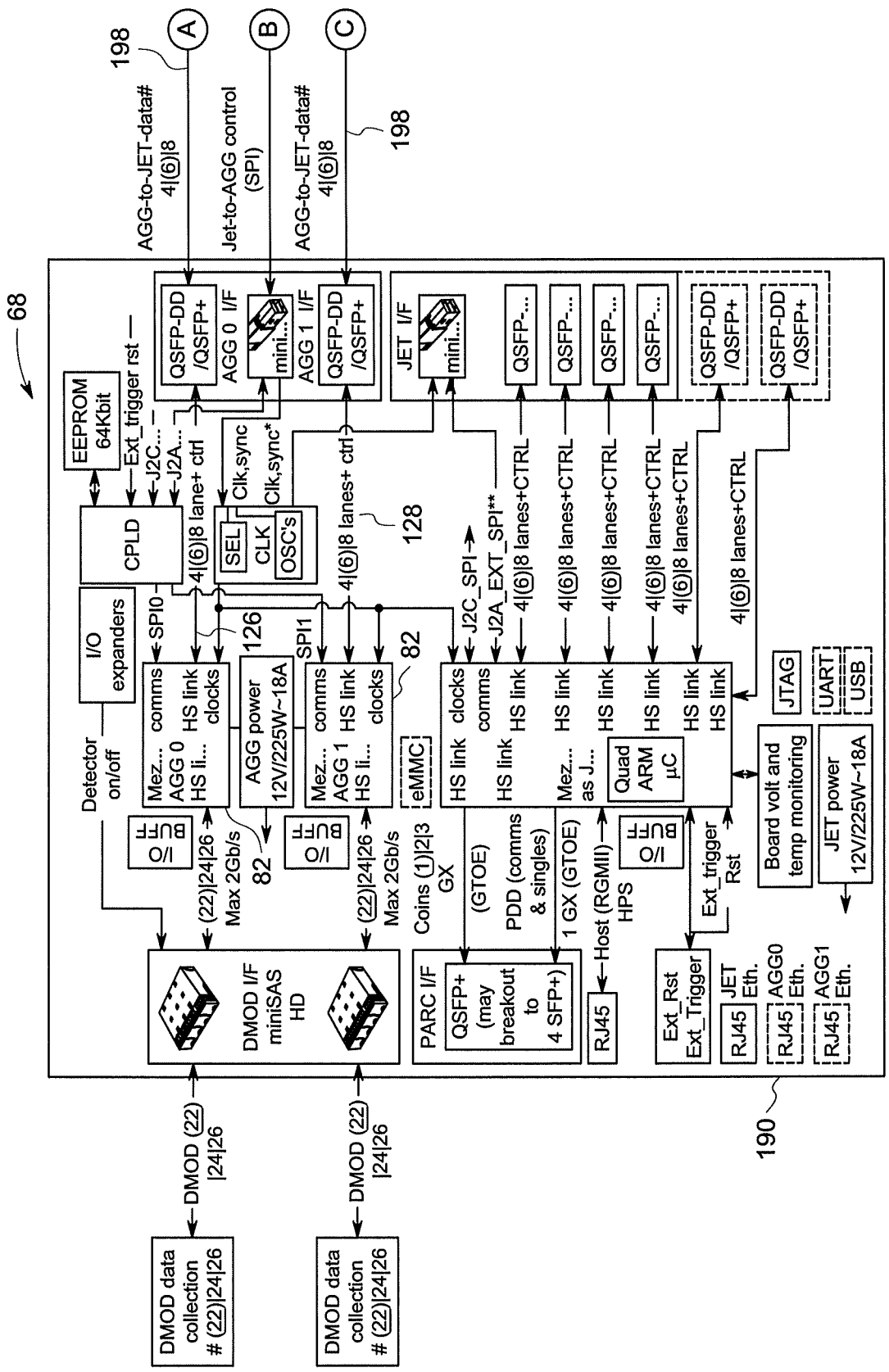
FIGS. 11A-11C are a schematic view of a plurality of data collection boards in communication with a master data collection board, in accordance with aspects of the present disclosure.
Figure 11B:
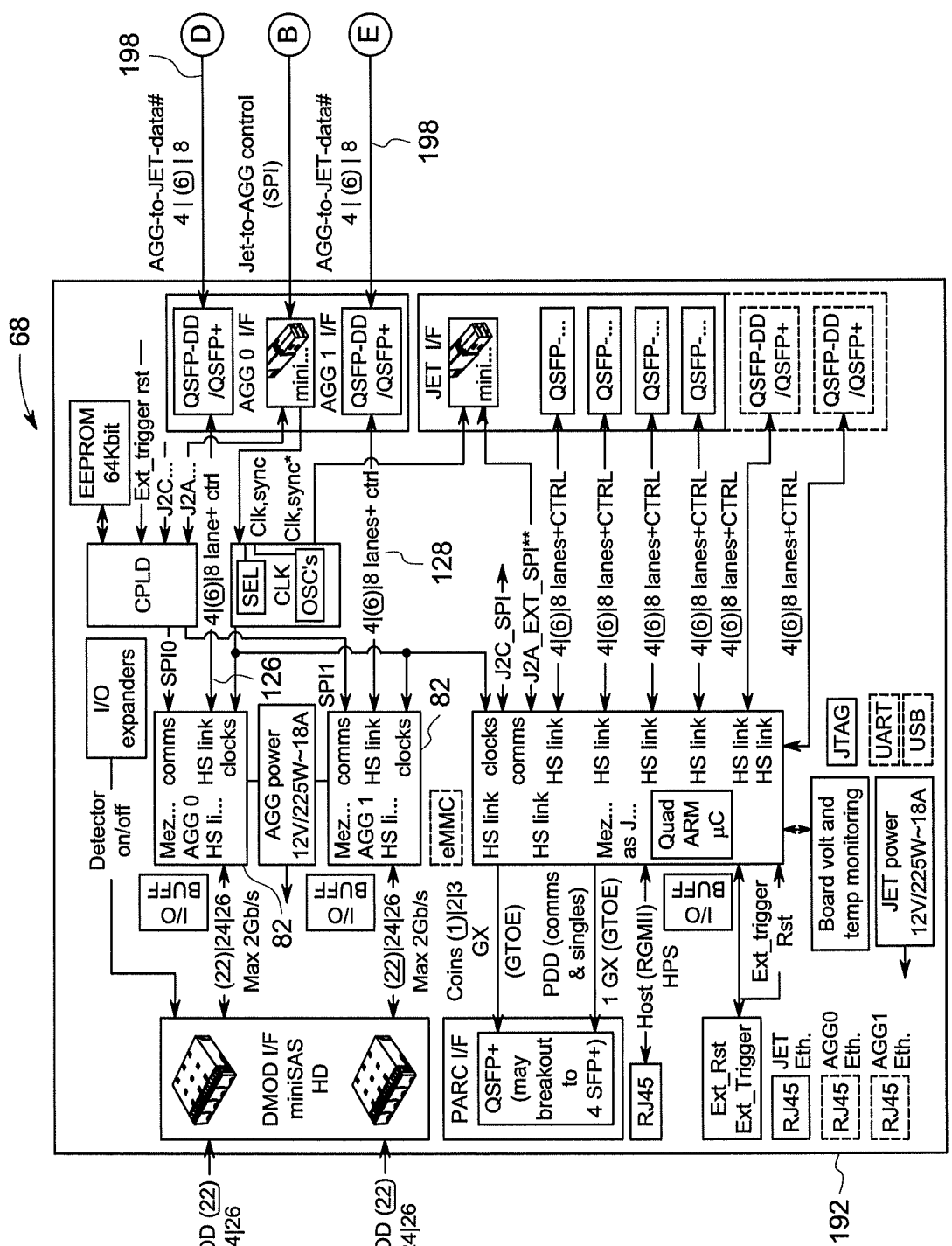
Figure 11C:
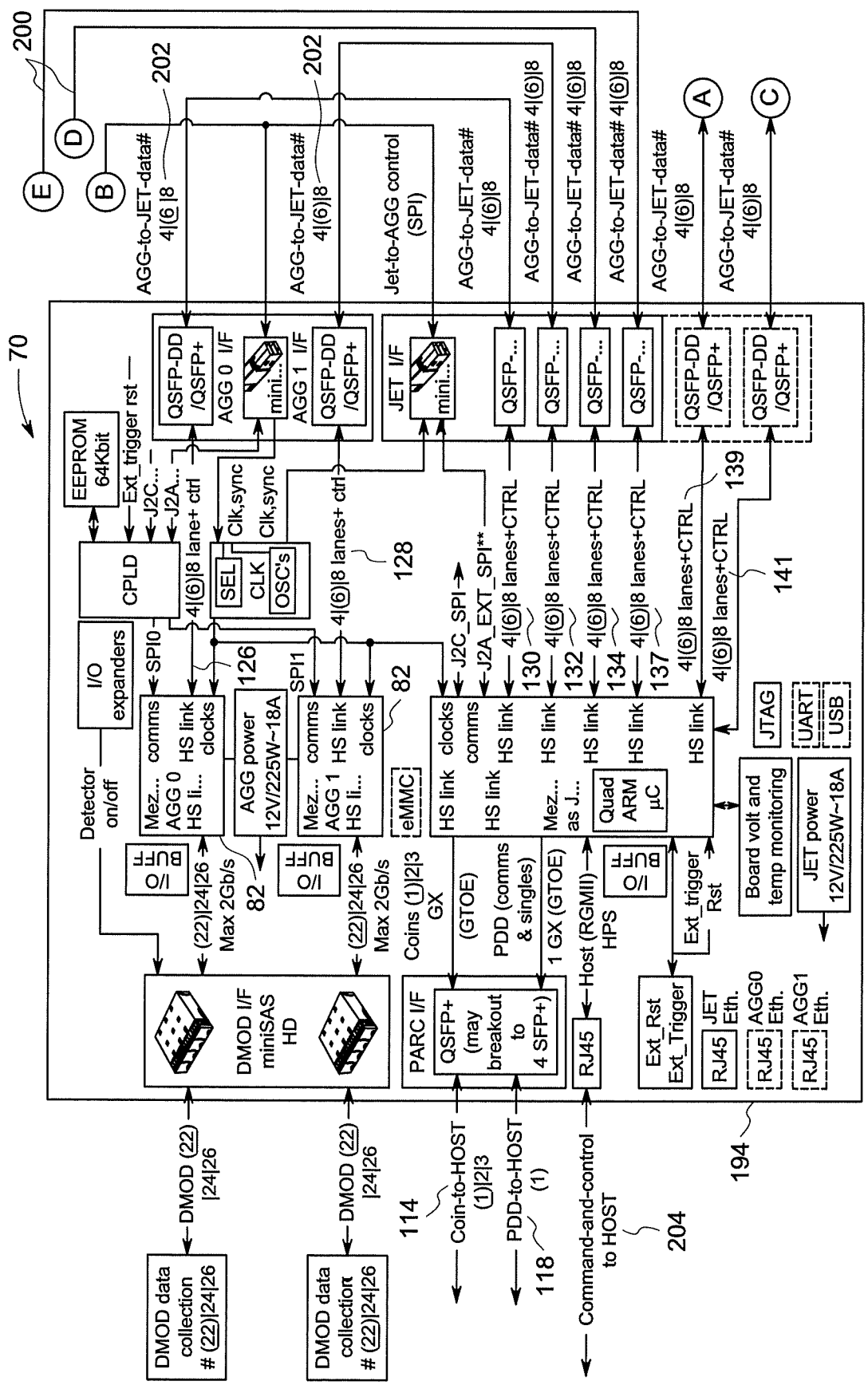

FIGS. 11A-11C are a schematic view of a plurality of the data collection boards 68 (e.g., data collection boards 190 and 192) in communication with the master data collection board 70 (e.g., for a modular gantry having three gantry segments 46 and a patient axial FOV of approximately 192 cm). The data collection boards 68 and the master data collection board 70 are as described above and each coupled to a respective gantry segment of a modular gantry. The data collection boards 68 (e.g., aggregator data collection boards) collect the detector event data (e.g., event singles data) from the respective detector modules of the respective gantry segments they are coupled to. The master data collection board 70 aggregates or collects the detector event data from the detector modules of the gantry segment it is coupled to. In addition, the master data collection board 70 collects all of detector event data from each of the aggregator data collection boards 68. In particular, each aggregator data collection board 68 communicates the detector event data to the master data collection board 70 via one of its pairs 126 and 128 of transceivers 112 (shown on FIG. 7) on its respective mezzanine board 82 to the corresponding pair 134, 137, 139, and 141 of transceivers 112 (shown on FIG. 7) of the mezzanine board 82 of the master data collection board 70. Each aggregator data collection board 68 utilizes a different pair 134 and 137, or 139 and 141 of transceivers 112 (shown on FIG. 7) when communicating to a different corresponding pair of transceivers 112 (shown on FIG. 7) of the master data collection board 70. For example, the data collection board 190 may communicate via the pairs 126 and 128 of the transceivers 112 (shown on FIG. 7) with the master data collection board 70 pairs 139 and 141 as indicated by QSFP-DD cable 198. The data collection board 192 may communicate via the pairs 126 and 128 of the transceivers 112 (shown on FIG. 7) with the master data collection board 70 pairs 134 and 137 as indicated by QSFP-DD cable 200. In addition, the master data collection board 194 may communicate back onto itself for data collection, via the pairs 126 and 128 of the transceivers 112 (shown on FIG. 7) with the master data collection board 70 pairs 130 and 132, as indicated by QSFP-DD cable 202. Thus, through a serial connection the detector event data collected by a particular data collection board 68 may be communicated to the master data collection board 70 via any intervening data collection boards 68.

Further, the master data collection board 70 generates coincidence pairs from all of the detector event data collected from the three gantry segments. The master data collection board 70 transfers or communicates the coincidence data to the system host computer of the PET imaging system and/or PARC via the QSFP+ transceivers 114. The master data collection board 70 also transfers or communicates periodic detector data to the system host computer of the PET imaging system and/or PARC via the QSFP+ transceivers 118. The master data collection board 70 also transfers and communicates command and control data to/from the system host computer of the PET imaging system and/or PARC via the RJ45 Host transceivers as indicated by reference numeral 204.

In certain embodiments, only the master data collection board 70 performs coincidence event sorting on all of the detector event data collected from the three gantry segments. In certain embodiments, each of the data collection boards 68 and the master data collection board 70 do coincidence event sorting on the respective detector event data collected from the respective detector modules of the respective gantry segments they are coupled to.

The master data collection board 70 may also perform other functions related to detector event processing. For example, the master data collection board 70 may perform histogramming on the coincidence event sorted events, throttling (e.g., random dropping of events), and other functions related to coincidence processing.

Technical effects of the disclosed subject matter include providing a distributed data collection architecture for collecting data between multiple detector modules (e.g., rings of detector modules) and data aggregation circuit boards. The distributed data collection architecture allows for simplified data flow as PET scanners grow larger in axial FOV. In particular, the distributed data collection architecture is scalable so it can be reliably utilized with a PET scanner having a modular gantry that is also scalable (via assembling additional gantry segments) to increase the axial FOV.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

This written description uses examples to disclose the present subject matter, including the best mode, and also to enable any person skilled in the art to practice the invention, including making and using any devices or systems and performing any incorporated methods. The patentable scope of the present subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A distributed data collection architecture for a positron emission tomography (PET) imaging system, comprising:

a plurality of data collection boards, wherein each data collection board of the plurality of data collection boards is coupled to a respective gantry segment of the PET imaging system, wherein the PET imaging system comprises a modular gantry having a plurality of gantry segments that are physically separate from each other, and each gantry segment of the plurality of gantry segments comprises a plurality of detector modules coupled to a respective data collection board of the plurality of data collection boards; and wherein each respective data collection board of the plurality of data collection boards is configured to acquire all detector event data from a respective plurality of detector modules of the respective gantry segment the respective data collection board is coupled to, and only one data collection board of the plurality of data collection boards is configured to act as a master data collection board that collects all of the detector event data from each data collection board of the plurality of data collection boards and to generate coincidence pairs from all of the detector event data.

2. The distributed data collection architecture of claim 1, wherein each data collection board of the plurality of data collection boards comprises a mezzanine board, and each mezzanine board has a common hardware structure.

3. The distributed data collection architecture of claim 2, wherein each data collection board of the plurality of data collection boards is configured so that all outputs are outputted directly from the mezzanine board.

4. The distributed data collection architecture of claim 2, wherein each data collection board of the plurality of data collection boards except the master data collection board comprises the mezzanine board coupled to a carrier board.

5. The distributed data collection architecture of claim 1, wherein the plurality of detector modules in each gantry segment of the plurality of gantry segments is electrically coupled in a daisy-chain architecture.

6. The distributed data collection architecture of claim 1, wherein at least one data collection board of the plurality of data collection boards in addition to the master data collection board is configured to perform coincidence event sorting on the detector event data acquired from the respective gantry segment of the plurality of gantry segments that the at least one data collection board is coupled to.

7. The distributed data collection architecture of claim 1, wherein only the master data collection board is configured to perform coincidence event sorting on all of the detector event data collected from each data collection board of the plurality of data collection boards.

8. The distributed data collection architecture of claim 1, wherein each respective data collection board of the plurality of data collection boards is configured to distribute power to the respective plurality of detector modules of the respective gantry segment of the plurality of gantry segments that the respective data collection board is coupled to.

9. The distributed data collection architecture of claim 1, wherein the master data collection board is configured to provide a system-wide clock signal to the other data collection boards of the plurality of data collection boards, and each of the other data collection boards is configured to provide the system-wide clock signal to the respective plurality of detector modules of the respective gantry segment that the respective other data collection board is coupled to.

10. The distributed data collection architecture of claim 1, wherein the distributed data collection architecture is configured to be scalable for the modular gantry, wherein the modular gantry comprises two or more gantry segments of the plurality of gantry segments.

11. A positron emission tomography (PET) imaging system, comprising:
a modular gantry comprising a plurality of gantry segments that are physically separate from each other, wherein each gantry segment of the plurality of gantry segments comprises a plurality of detector modules; and
a distributed data collection architecture comprising a plurality of data collection boards, each respective data collection board of the plurality of data collection boards is coupled to a respective plurality of detector modules of a respective gantry segment of the plurality of gantry segments, each respective data collection board comprises a mezzanine board, each mezzanine board has a common hardware structure, and only one data collection board of the plurality of data collection boards is configured to act as a master data collection board that collects all detector event data from each data collection board of the plurality of data collection boards and to generate coincidence pairs from all of the detector event data.

12. The PET imaging system of claim 11, wherein each respective data collection board of the plurality of data collection boards is configured to acquire all detector event data from a respective plurality of detector modules of the respective gantry segment the respective data collection board is coupled to.

13. The PET imaging system of claim 12, wherein at least one data collection board of the plurality of data collection boards in addition to the master data collection board is configured to perform coincidence event sorting on the detector event data acquired from the respectively gantry segment of the plurality of gantry segments that the at least one data collection board is coupled to.

14. The PET imaging system of claim 12, wherein only the master data collection board is configured to perform coincidence event sorting on all of the detector event data collected from each data collection board of the plurality of data collection boards.

15. The PET imaging system of claim 11, wherein each data collection board of the plurality of data collection boards is configured so that all outputs are outputted directly from the mezzanine board.

16. The PET imaging system of claim 11, wherein each data collection board of the plurality of data collection boards except the master data collection board comprises the mezzanine board coupled to a carrier board.

17. The PET imaging system of claim 11, wherein the distributed data collection architecture is configured to be scalable for the modular gantry, wherein the modular gantry comprises two or more gantry segments of the plurality of gantry segments.

18. The PET imaging system of claim 11, wherein the master data collection board is configured to provide a system-wide clock signal to the other data collection boards of the plurality of data collection boards, and each of the other data collection boards is configured to provide the system-wide clock signal to the respective plurality of detector modules of the respective gantry segment that the respective other data collection board is coupled to.

19. The PET imaging system of claim 11, wherein the plurality of data collection boards is electrically coupled in a daisy-chain architecture.

20. A set of data collection boards for a distributed data collection architecture for a positron emission tomography (PET) imaging system, comprising:
- a first data collection board configured to couple to a first plurality of detector modules of a first gantry segment of the PET imaging system, wherein the PET imaging system comprises a modular gantry having a plurality of gantry segments that are physically separate from each other, and the first data collection board comprises a first mezzanine board; and
- a second data collection board configured to couple to a second plurality of detector modules of a second gantry segment of the PET imaging system, and the second data collection board comprises a second mezzanine board having a same hardware architecture as the first mezzanine board; and
- wherein the first data collection board is configured to acquire all detector event data from the first plurality of detector modules, and the second data collection board is configured to acquire all detector event data from the second plurality of detector modules, to collect all the detector event data from the first plurality of detector modules via the first data collection board, and to generate coincidence pairs from all of the detector event data collected from both the first plurality of detector modules and the second plurality of detector modules.

* * * * *